United States Patent
Ye et al.

(10) Patent No.: US 10,627,469 B2
(45) Date of Patent: Apr. 21, 2020

(54) METHOD OF REMOVING GHOST ARTIFACTS FROM MAGNETIC RESONANCE IMAGE, AND MAGNETIC RESONANCE APPARATUS THEREFOR

(71) Applicant: Korea Advanced Institute of Science and Technology, Daejeon (KR)

(72) Inventors: Jong Chul Ye, Daejeon (KR); Ju Young Lee, Daejeon (KR); Kyong Hwan Jin, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 567 days.

(21) Appl. No.: 15/323,644

(22) PCT Filed: Feb. 5, 2016

(86) PCT No.: PCT/KR2016/001279
§ 371 (c)(1),
(2) Date: Jan. 3, 2017

(87) PCT Pub. No.: WO2017/069347
PCT Pub. Date: Apr. 27, 2017

(65) Prior Publication Data
US 2017/0299680 A1    Oct. 19, 2017

(30) Foreign Application Priority Data

Oct. 20, 2015    (KR) .................. 10-2015-0146208

(51) Int. Cl.
*G01R 33/56* (2006.01)
*A61B 5/055* (2006.01)
(Continued)

(52) U.S. Cl.
CPC .......... *G01R 33/5608* (2013.01); *A61B 5/055* (2013.01); *G01R 33/4818* (2013.01);
(Continued)

(58) Field of Classification Search
CPC ............ G01R 33/4818; G01R 33/5602; G01R 33/5608; G01R 33/56554; G01R 33/5616; G01R 33/5611; A61B 5/055
See application file for complete search history.

(56) References Cited

U.S. PATENT DOCUMENTS

| | | | | |
|---|---|---|---|---|
| 5,910,728 A * | 6/1999 | Sodickson | ......... | G01R 33/3815 324/309 |
| 6,697,507 B1 * | 2/2004 | Chapman | ............. | G01R 33/565 382/107 |
| 2015/0091570 A1 * | 4/2015 | Gross | ................. | G01R 33/5608 324/309 |

FOREIGN PATENT DOCUMENTS

| | | |
|---|---|---|
| JP | 2005144173 | 6/2005 |
| JP | 2008154887 | 7/2008 |

(Continued)

OTHER PUBLICATIONS

Lee et al., Reference-Free Single-Pass EPI Nyquist Ghost CorrectionUsing Annihilating Filter-Based Low Rank HankelMatrix (ALOHA), Magnetic Resonance in Medicine 76:1775-1789, 2016.*
(Continued)

*Primary Examiner* — Bo Joseph Peng
(74) *Attorney, Agent, or Firm* — Hodgson Russ LLP (57) ABSTRACT

A method of reconstructing a magnetic resonance image includes receiving echo planar imaging (EPI) data, acquiring an even scan line image and an odd scan line image from k-space data of the EPI data, and reconstructing missing portions of the even scan line image and the odd scan line image.

14 Claims, 9 Drawing Sheets (51) Int. Cl.
*G01R 33/565* (2006.01)
*G01R 33/48* (2006.01)
*G01R 33/561* (2006.01)

(52) U.S. Cl.
CPC ..... *G01R 33/5602* (2013.01); *G01R 33/5616* (2013.01); *G01R 33/56554* (2013.01); *G01R 33/5611* (2013.01)

(56) References Cited

FOREIGN PATENT DOCUMENTS

| JP | 2009082178 | 4/2009 |
| KR | 20120138478 | 12/2012 |
| KR | 20140122991 | 10/2014 |

OTHER PUBLICATIONS

EPO, Office Action for EP Application No. 16857605, dated Oct. 8, 2018.
Chen et al., "High Spatial-Temporal-Resolution fMRI with Odd- and Even-Fourier EPI and Two-Way Hermitian Reconstruction," Proc. Intl. Soc. Mag. Reson. Med., vol. 11, Jul. 10, 2003, p. 1743.
Li et al., "Parallel EPI artifact correction (PEAC) for N/2 ghost suppression in neuroimaging applications," Magnetic Resonance Imaging, vol. 31, Issue 6, Elsevier Inc., Apr. 16, 2013, pp. 1022-1028.
Jin et al., "Recent Progresses of Accelerated MRI Using Annihilating Filter-Based Low-Rank Interpolation," 2016 IEEE International Conference on Image Processing (ICIP), Sep. 25, 2016, pp. 968-972.

\* cited by examiner

METHOD OF REMOVING GHOST ARTIFACTS FROM MAGNETIC RESONANCE IMAGE, AND MAGNETIC RESONANCE APPARATUS THEREFOR

TECHNICAL FIELD

Embodiments relate to a method of removing ghost artifacts from echo planar imaging (EPI) data acquired by a magnetic resonance imaging (MRI) apparatus using EPI technology.

BACKGROUND ART

Magnetic resonance imaging (MRI) is a technology that images an inside of a human body based on signals collected by resonating elements arranged in a predetermined magnetic field using radio frequency (RF) pulses. In general, magnetic resonance images may be acquired at a super high speed using echo planar imaging (EPI) technology. EPI technology may receive a magnetic resonance image in a single free induction decay (FID) signal for 40 to 100 milliseconds (ms), thereby implementing super high-speed imaging technology. Fast scanning of EPI may reduce issues relating to MRI or defects resulting from a movement of a target. However, EPI technology may generate a large field gradient magnetic field and perform switching at a rate of about 1 kilohertz (kHz), and thus it may be difficult to implement images using hardware and serious image distortion may occur due to magnetic susceptibility of the target.

Unlike other methods that read data in a predetermined direction, EPI technology reads data from an even scan line and an odd scan line in a k-space in different directions, and thus a phase difference may occur between the lines. The phase difference causes ghost artifacts in an image domain, and the ghost artifacts obstruct an appropriate analysis of EPI images. Thus, research on methods of removing ghost artifacts has been conducted.

A reference scan may be acquired before a reconstructed image is acquired, and a phase difference between an even scan line and an odd scan line in a k-space may be calculated to correct a phase difference in a target image. However, it takes a longer time since an additional image is needed. Thus, when using the foregoing method, only three scan lines are acquired from the additional image for correction to overcome the disadvantage in time. However, ghost artifacts still may not be removed suitably due to coil sensitivity in an MRI apparatus Further, an additional image to offset ghost artifacts may be acquired by correcting a sequence to be used to acquire an EPI image. However, it also takes time since another additional image needs to be acquired further.

DISCLOSURE OF INVENTION

Technical Goals

An aspect provides a technology to remove ghost artifacts from an echo planar imaging (EPI) image acquired by a magnetic resonance imaging (MRI) apparatus without acquiring a reference scan when reconstructing a magnetic resonance image.

Technical Solutions

According to an aspect, there is provided a method of reconstructing a magnetic resonance image, the method including receiving echo planar imaging (EPI) data, acquiring an even scan line image and an odd scan line image from k-space data of the EPI data, and reconstructing missing portions of the even scan line image and the odd scan line image.

The reconstructing of the missing portions of the even scan line image and the odd scan line image may include reconstructing the missing portions by constructing block Hankel matrices from the even scan line image and the odd scan line image based on a presence of an annihilation filter in a k-space and interpolating Fourier data yet to be measured through a low rank matrix completion algorithm.

The reconstructing of the missing portions by constructing the block Hankel matrices from the even scan line image and the odd scan line image may include transforming the even scan line image and the odd scan line image into the block Hankel matrices using a commutative rule of a convolution operation of the k-space and the annihilation filter in a frequency domain.

The method may further include generating a single reconstructed image by combining the reconstructed even scan line image and the reconstructed odd scan line image.

The generating of the single reconstructed image may include generating the single reconstructed image using a sum of squares of the reconstructed even scan line image and the reconstructed odd scan line image.

The reconstructing of the missing portions of the even scan line image and the odd scan line image may include reconstructing the even scan line image and the odd scan line image using a plurality of minimum rank matrix completion algorithms after changing pyramid patches, each having a pyramidal structure, into block Hankel matrices.

The reconstructing of the images using the pyramid patches may include reconstructing the even scan line image and the odd scan line image through the matrix completion algorithms, reducing sizes of the pyramid patches, and reconstructing a low-frequency domain of a k-space through the matrix completion algorithms using values of the reconstructed even scan line image and the reconstructed odd scan line image as initial values.

The reconstructing of the images using the pyramid patches may include applying a stop reference less than or equal to a preset reference to a pyramid patch including noise greater than or equal to the preset reference, and applying a stop reference greater than or equal to the preset reference to a pyramid patch from which a low-frequency domain is cut off, among the pyramid patches, each having the pyramidal structure.

The EPI data may include at least one of single-coil EPI data or multi-coil EPI data.

The reconstructing of the missing portions of the even scan line image and the odd scan line image may include reconstructing the missing portions by assigning a weighting to a k-space of each of the even scan line image and the odd scan line image and constructing block Hankel matrices from the weighted even scan line image and the weighted odd scan line image.

According to another aspect, there is also provided an apparatus for reconstructing a magnetic resonance image, the apparatus including a processor configured to acquire an even scan line image and an odd scan line image from k-space data of EPI data, and reconstruct missing portions of the even scan line image and the odd scan line image.

The processor may be configured to reconstruct the missing portions by constructing block Hankel matrices from the even scan line image and the odd scan line image based on a presence of an annihilation filter in a k-space and interpolating Fourier data yet to be measured through a low rank matrix completion algorithm.

The processor may be configured to transform the even scan line image and the odd scan line image into the block Hankel matrices using a commutative rule of a convolution operation of the k-space and the annihilation filter in a frequency domain.

The processor may be configured to generate a single reconstructed image by combining the reconstructed even scan line image and the reconstructed odd scan line image.

The processor may be configured to generate the single reconstructed image using a sum of squares of the reconstructed even scan line image and the reconstructed odd scan line image.

The processor may be configured to reconstruct the even scan line image and the odd scan line image using a plurality of minimum rank matrix completion algorithms after changing pyramid patches, each having a pyramidal structure, into block Hankel matrices.

The processor may be configured to reconstruct the even scan line image and the odd scan line image through the matrix completion algorithms, reduce sizes of the pyramid patches, and reconstruct a low-frequency domain of a k-space through the matrix completion algorithms using values of the reconstructed even scan line image and the reconstructed odd scan line image as initial values.

The processor may be configured to apply a stop reference less than or equal to a preset reference to a pyramid patch including noise greater than or equal to the preset reference, and apply a stop reference greater than or equal to the preset reference to a pyramid patch from which a low-frequency domain is cut off, among the pyramid patches, each having the pyramidal structure.

The processor may be configured to reconstruct the missing portions by assigning a weighting to a k-space of each of the even scan line image and the odd scan line image and constructing block Hankel matrices from the weighted even scan line image and the weighted odd scan line image.

Effects

According to an embodiment, ghost artifacts may be removed from a magnetic resonance image without acquiring a reference scan from an echo planar imaging (EPI) image.

According to an embodiment, ghost artifacts may be removed only based on single-coil data, without using multi-coil data.

According to an embodiment, ghost artifacts may be removed effectively, whereby more precise results of functional magnetic resonance imaging (fMRI) analysis may be obtained.

BEST MODE

Hereinafter, embodiments will be described in detail with reference to the accompanying drawings.

Figure 1:
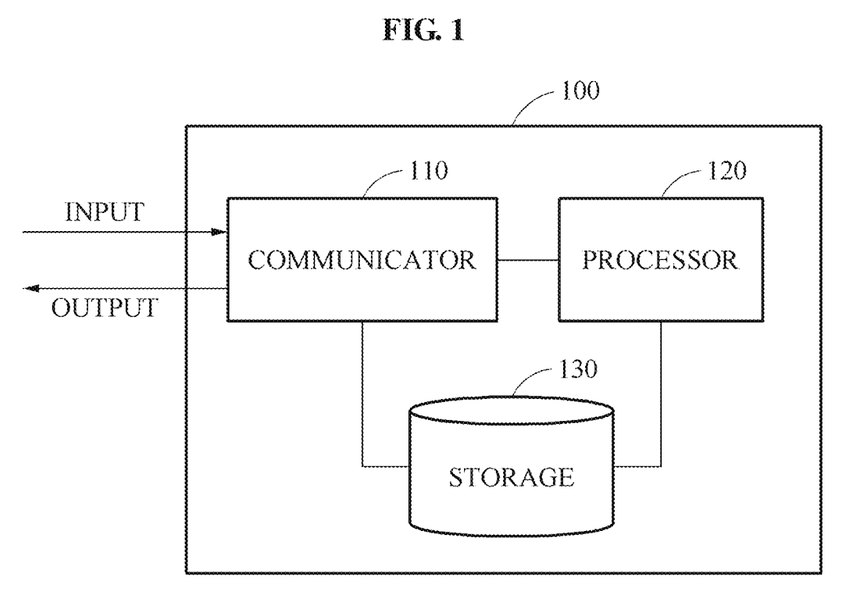
FIG. 1 is a block diagram illustrating an apparatus for reconstructing a magnetic resonance image according to an embodiment.

FIG. 1 is a block diagram illustrating an apparatus for reconstructing a magnetic resonance image according to an embodiment.

Referring to FIG. 1, an apparatus 100 for reconstructing a magnetic resonance image may include a communicator 110, a processor 120, and a storage 130.

The apparatus 100 may correct ghost artifacts in an echo planar imaging (EPI) image. Removal of the ghost artifacts may transform k-space data, separated into an even scan line image and an odd scan line image, into rank deficiency by constructing block Hankel matrices of the even scan line image and the odd scan line image based on a presence of an annihilation filter in a k-space. In this example, the apparatus 100 may solve the rank deficiency through various low rank matrix completion algorithms.

The communicator 110 may receive EPI data from a magnetic resonance imaging (MRI) scanner (not shown). The communicator may receive the EPI data from the MRI scanner in a wireless or wired manner.

The EPI data may include at least one of single-coil EPI data or multi-coil EPI data.

The communicator 110 may output a reconstructed magnetic resonance image to an output device so that a user may view the magnetic resonance image.

The processor 120 may acquire an even scan line image and an odd scan line image from the k-space data of the received EPI data.

The processor 120 may reconstruct missing portions of the even scan line image and the odd scan line image.

The processor 120 may reconstruct the missing portions by interpolating Fourier data yet to be measured since the k-space data is transformed into the rank deficiency by constructing respective block Hankel matrices of the even scan line image and the odd scan line image based on the presence of the annihilation filter in the k-space. Here, the processor 120 may solve the rank deficiency through a plurality of low rank matrix completion algorithms.

The processor 120 may transform the even scan line image and the odd scan line image into the respective block Hankel matrices using a commutative rule of a convolution operation of the k-space and the annihilation filter in a frequency domain.

The processor 120 may generate a single reconstructed image by combining the reconstructed even scan line image and the reconstructed odd scan line image. In this example, the processor 120 may generate the single reconstructed image using a sum of squares of the reconstructed even scan line image and the reconstructed odd scan line image.

The processor 120 may reconstruct the even scan line image and the odd scan line image using a plurality of minimum rank matrix completion algorithms after changing pyramid patches, each having a pyramidal structure, into block Hankel matrices.

The processor 120 may reconstruct the even scan line image and the odd scan line image through the matrix completion algorithms, reduce sizes of the pyramid patches, and reconstruct a low-frequency domain of the k-space through the matrix completion algorithms using values of the reconstructed even scan line image and the reconstructed odd scan line image as initial values.

In this example, the processor 120 may apply a stop reference less than or equal to a preset reference to a pyramid patch including noise greater than or equal to the preset reference, and apply a stop reference greater than or equal to the preset reference to a pyramid patch from which a low-frequency domain is cut off, among the pyramid patches, each having the pyramidal structure.

The processor 120 may reconstruct the missing portions by assigning a weighting to a k-space of each of the even scan line image and the odd scan line image and constructing block Hankel matrices from the weighted even scan line image and the weighted odd scan line image. Here, the weighting may be determined based on a characteristic of sparsifying transform of an EPI image. Thus, the processor 120 may sparsely transform an EPI image by assigning the weighting to the k-space data before the block Hankel matrices are constructed.

The storage 130 may arbitrarily store the EPI image received at the communicator 110, and also store the image reconstructed by the processor 120.

Figure 2:
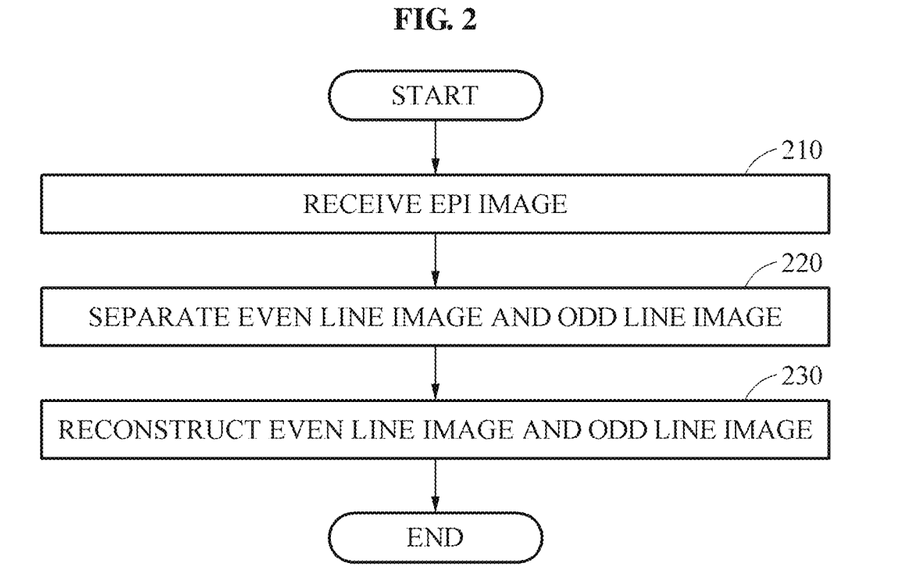
FIG. 2 is a flowchart illustrating a method of reconstructing a magnetic resonance image according to an embodiment.

FIG. 2 is a flowchart illustrating a method of reconstructing a magnetic resonance image according to an embodiment.

In operation 210, an apparatus for reconstructing a magnetic resonance image may receive an EPI image.

In operation 220, the apparatus for reconstructing a magnetic resonance image may separate an even scan line image and an odd scan line image from a k-space of the received EPI image.

In operation 230, the apparatus for reconstructing a magnetic resonance image may reconstruct missing portions of the even scan line image and the odd scan line image.

In this example, the apparatus for reconstructing a magnetic resonance image may transform k-space data, separated into an even scan line image and an odd scan line image, into rank deficiency by constructing block Hankel matrices of the even scan line image and the odd scan line image based on a presence of an annihilation filter in a k-space. Here, the rank deficiency may be solved through a plurality of low rank matrix completion algorithms. The apparatus for reconstructing a magnetic resonance image may reconstruct the missing portions by interpolating Fourier data yet to be measured through the low rank matrix completion algorithms since the k-space data is transformed into the rank deficiency by constructing respective block Hankel matrices of the even scan line image and the odd scan line image based on the presence of the annihilation filter in the k-space.

The apparatus for reconstructing a magnetic resonance image may transform the even scan line image and the odd scan line image into the block Hankel matrices using a commutative rule of a convolution operation of the k-space and the annihilation filter in a frequency domain.

The apparatus for reconstructing a magnetic resonance image may reconstruct the missing portions by assigning a weighting to a k-space of each of the even scan line image and the odd scan line image and constructing block Hankel matrices from the weighted even scan line image and the weighted odd scan line image. Here, the weighting may be determined based on a characteristic of sparsifying transform of an EPI image. Thus, the apparatus for reconstructing a magnetic resonance image may sparsely transform the EPI image before the block Hankel matrices are constructed. The apparatus for reconstructing a magnetic resonance image may reconstruct the even scan line image and the odd scan line image using a plurality of minimum rank matrix completion algorithms after changing pyramid patches, each having a pyramidal structure, into block Hankel matrices. In this example, the apparatus for reconstructing a magnetic resonance image may reconstruct the even scan line image and the odd scan line image through the matrix completion algorithms, reduce sizes of the pyramid patches, and reconstruct a low-frequency domain of the k-space through the matrix completion algorithms using values of the reconstructed even scan line image and the reconstructed odd scan line image as initial values.

The apparatus for reconstructing a magnetic resonance image may generate a single reconstructed image by combining the reconstructed even scan line image and the reconstructed odd scan line image.

The apparatus for reconstructing a magnetic resonance image may generate the single reconstructed image using a sum of squares of the reconstructed even scan line image and the reconstructed odd scan line image.

Figure 3:
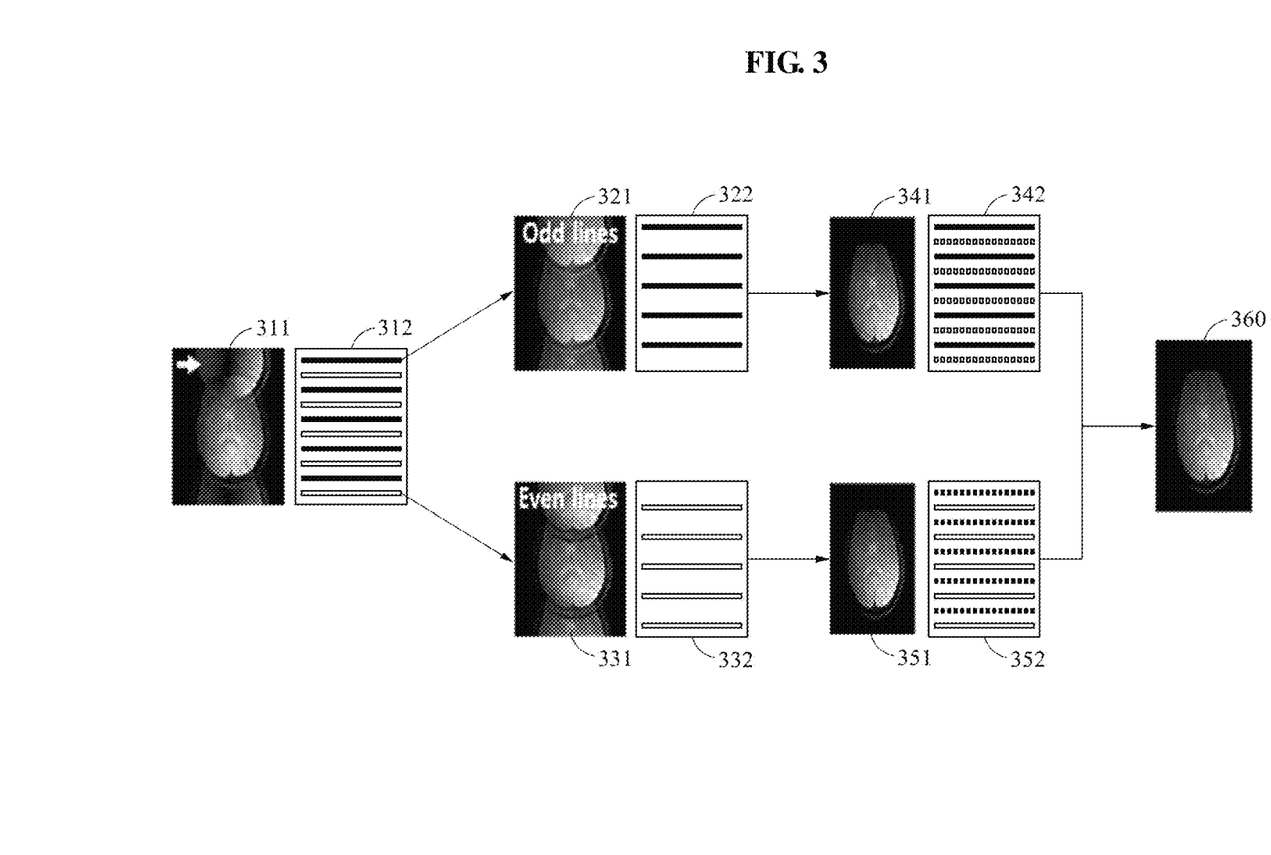
FIG. 3 illustrates a method of reconstructing a magnetic resonance image using a k-space according to an embodiment.

FIG. 3 illustrates a method of reconstructing a magnetic resonance image using a k-space according to an embodiment.

Referring to FIG. 3, an apparatus for reconstructing a magnetic resonance image may separate an even scan line image 321, 322 and an odd scan line image 331, 332 from a k-space 312 of an EPI image 311.

The apparatus for reconstructing a magnetic resonance image may acquire a reconstructed even scan line image 341, 342 by reconstructing the even scan line image 321, 322, and acquire a reconstructed odd scan line image 351, 352 by reconstructing the odd scan line image 331, 332.

The apparatus for reconstructing a magnetic resonance image may acquire a final image 360 from which ghost artifacts are removed, by combining the reconstructed even scan line image 341, 342 and the reconstructed odd scan line image 351, 352.

The series of operations may be described using the following equations.

The EPI image may be expressed using Equation 1.

$$S_n(k_x, k_y) = \iint m(x, y) e^{j2\pi\left[\Delta f(x,y)\left((TE+(n-\frac{N}{2})ESP)+(-1)^n\left(\frac{k_x}{\gamma G_x}\right)\right)+k_x x+k_y y\right]} dxdy \quad \text{[Equation 1]}$$

In Equation 1, m denotes an intensity of the image, and $\Delta f$ denotes a frequency offset resulting from field inhomogeneity. x and y denote a direction of read-out and a direction of phase encoding, respectively. TE denotes an echo time, and ESP denotes a time interval between echoes. N denotes a total number of echoes, and n denotes an index of each echo line.

A model of Equation 1 includes ghost artifacts resulting from a phase difference between echo lines. A value of $(-1)^n$ may vary based on whether n is an even number or an odd number. Thus, an even scan line and an odd scan line may have different polarities, which may be represented using virtual k-spaces, as expressed by Equation 2.

$$S_{n,+}(k_x, k_y) = \iint m(x,y) e^{j2\pi\left[\Delta f(x,y)\left((TE+(n-\frac{N}{2})ESP)+\left(\frac{k_x}{\gamma G_x}\right)\right)+k_x x+k_y y\right]} dxdy$$

$$S_{n,-}(k_x, k_y) = \iint m(x,y) e^{j2\pi\left[\Delta f(x,y)\left((TE+(n-\frac{N}{2})ESP)-\left(\frac{k_x}{\gamma G_x}\right)\right)+k_x x+k_y y\right]} dxdy$$

[Equation 2]

In Equation 2, $S_{n,+}(k_x,k_y)$ denotes a k-space in which even scan lines are collected, and $S_{n,-}(k_x,k_y)$ denotes a k-space in which odd scan lines are collected. The two separate k-spaces include missing odd scan lines and missing even scan lines, respectively, and thus may be regarded as being downsampled by a factor of 2. Accordingly, the method of reconstructing a magnetic resonance image may change into an issue of filling in the missing portions of the k-spaces.

One equation in Equation 2 may be subtracted from the other equation, as expressed by Equation 3.

$$S_{n,\Delta}(k_x, k_y) = S_{n,-}(k_x, k_y) - S_{n,+}(k_x, k_y)$$

$$= \iint A(x,y) \left( e^{-j2\pi\Delta f(x,y)\frac{k_x}{\gamma G_x}} - e^{j2\pi\Delta f(x,y)\frac{k_x}{\gamma G_x}} \right) e^{j2\pi(k_x x + k_y y)} dxdy$$

$$= -\iint A(x,y) 2j\sin\left(2\pi\Delta f(x,y)\frac{k_x}{\gamma G_x}\right) e^{j2\pi(k_x x+k_y y)} dxdy$$

where $A = m(x,y) e^{j2\pi[\Delta f(x,y)((TE+(n-\frac{N}{2})ESP))]}$

[Equation 3]

In a case in which the frequency offset is sufficiently insignificant, Equation 3 may be approximated as expressed by Equation 4.

$$S_{n,\Delta}(k_x, k_y) \simeq -j2\pi k_x \iint \frac{2}{\gamma G_x} A(x,y)\Delta f(x,y) e^{j2\pi(k_x x + k_y y)} dxdy = \frac{2}{\gamma G_x} \mathcal{F}\left[\frac{\partial A(x,y)\Delta f(x,y)}{\partial x}\right]$$

[Equation 4]

Equation 4 may be the same as a result of performing Fourier transform on a gradient of a product of an RF offset and an image. Since $A(x,y)\Delta f(x,y)$ has a smooth gradient and $S_{n,\Delta}(k_x,k_y)$ has a sparse density, a difference $S_{n,\Delta}$ between the k-space using the odd lines and the k-space using the even lines may be sparse. A Hankel matrix constructed based on $S_{n,\Delta}(k_x,k_y)$ may be ranked low. Accordingly, an annihilation filter that satisfies Equation 5 may be present.

$$\mathcal{H}(S_{n,\Delta})\mathfrak{h}=0$$

[Equation 5]

In Equation 5, $\mathcal{H}(S_{n,\Delta})$ denotes a Hankel matrix constructed from $S_{n,\Delta}$, and $\mathfrak{h}$ denotes a vectorized form of a two-dimensional (2D) annihilation filter. In this example, $S_{n,\Delta}=S_{n,-}-S_{n,+}$ is satisfied and thus, a relationship as expressed by Equation 6 may be obtained.

$$(\mathcal{H}(S_{n,-}) - \mathcal{H}(S_{n,+}))\mathfrak{h} = 0 \Longleftrightarrow \mathcal{Y}\begin{bmatrix}\mathfrak{h}\\-\mathfrak{h}\end{bmatrix}$$

where, $\mathcal{Y} = [\mathcal{H}(S_{n,-})\ \mathcal{H}(S_{n,+})]$

[Equation 6]

Accordingly, a matrix $\mathcal{Y}$ may be generated by constructing respective block Hankel matrices from the k-space including the even scan lines and the k-space including the odd scan lines and combining the two matrices. A low rankness of the matrix $\mathcal{Y}$ may be used to fill in the missing portions of the data.

When the missing portions of $S_{n,+}$ and $S_{n,-}$ are filled in and reconstructed, a final image without ghost artifacts may be generated by combining the reconstructed even scan line image and the reconstructed odd scan line image. In this example, the reconstructed even scan line image and the odd scan line image may be combined using a sum of squares.

In a case of using multi-coil data, restoration may be performed similarly by constructing a Hankel matrix, as expressed by Equation 6.

$$\mathcal{Y}^{(P)} = [\mathcal{Y}^{(1)} \ldots \mathcal{Y}^{(p)}]$$

[Equation 7]

In Equation 7, $\mathcal{Y}^{(i)}$ denotes a Hankel matrix at an i-th coil.

Figure 4:
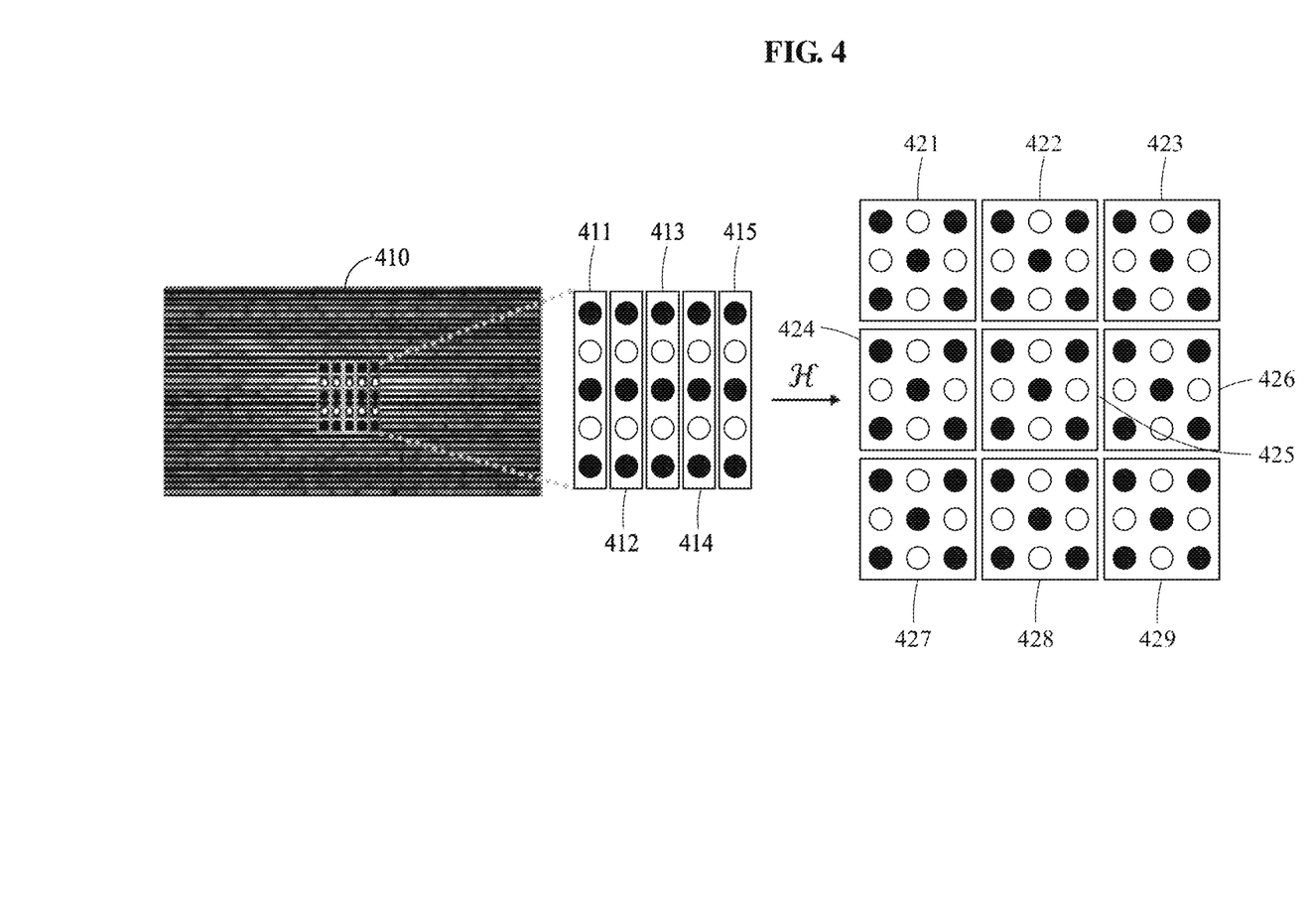
FIG. 4 illustrates a method of constructing block Hankel matrices from a k-space in which data is insufficient according to an embodiment.

FIG. 4 illustrates a method of constructing block Hankel matrices from a k-space in which data is insufficient according to an embodiment.

Referring to FIG. 4, patches 411, 412, 413, 414, and 415 may be extracted from a k-space 410 of an EPI image. Here, each patch includes filled odd scan lines and missing even scan lines.

In this example, an apparatus for reconstructing a magnetic resonance image may construct a Hankel matrix or Hankel matrices for each patch. In detail, the apparatus for reconstructing a magnetic resonance image may construct a Hankel matrix 421 for the patch 411, Hankel matrices 422 and 424 for the patch 412, Hankel matrices 423, 425, and 427 for the patch 413, Hankel matrices 426 and 428 for the patch 414, and a Hankel matrix 429 for the patch 415. Rank deficiency of the Hankel matrices may be used to reconstruct data of the missing portions.

Figure 5:
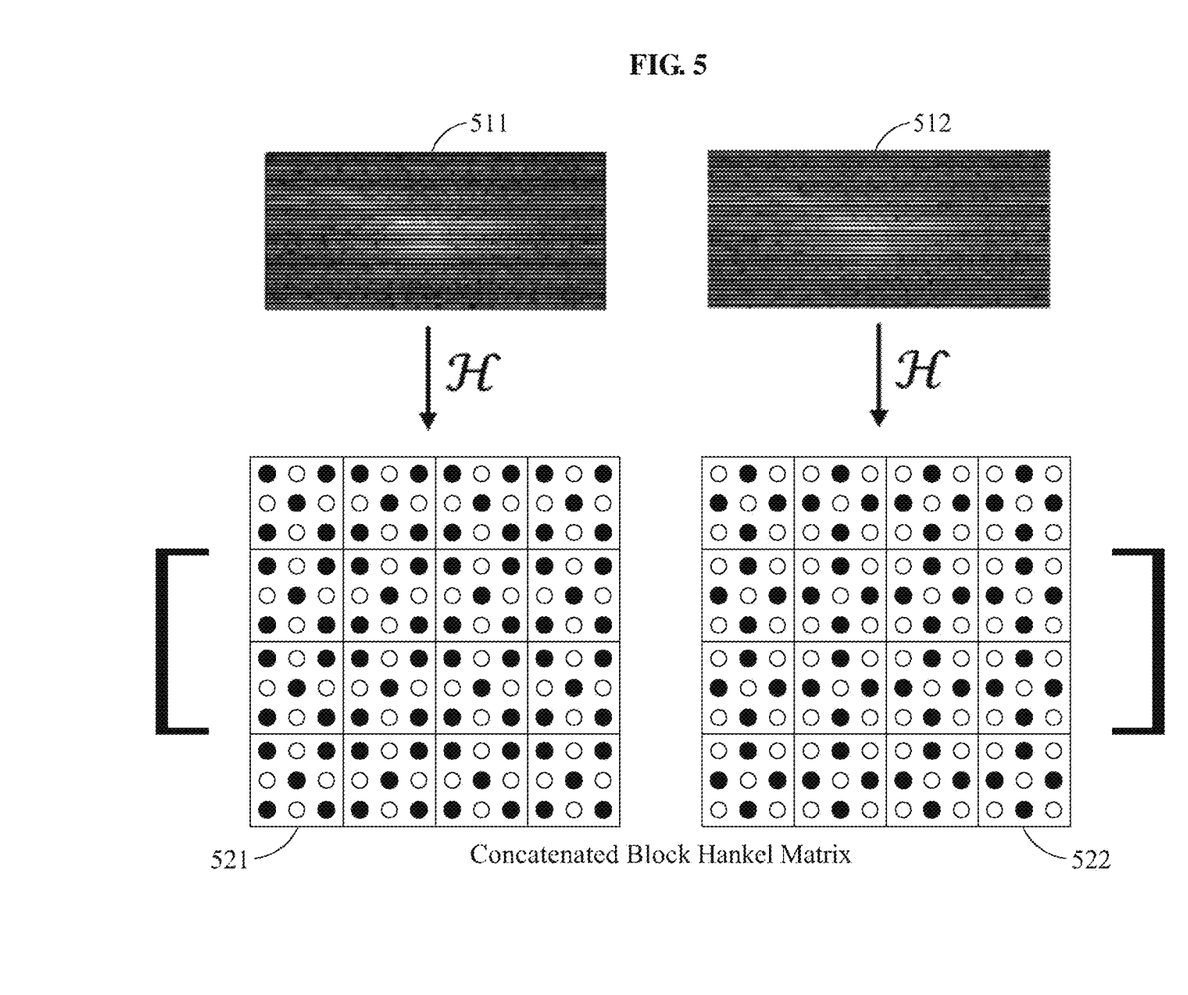
FIG. 5 illustrates a result of constructing a block Hankel matrix from each of an even scan line image and an odd scan line image according to an embodiment.

FIG. 5 illustrates a result of constructing a block Hankel matrix from each of an even scan line image and an odd scan line image according to an embodiment.

Referring to FIG. 5, a Hankel matrix 521 may be constructed from EPI data 511, and a Hankel matrix 522 may be constructed from EPI data 512.

An apparatus for reconstructing a magnetic resonance image may fill in and reconstruct missing portions in each of the Hankel matrices 521 and 522, and generate a final image without ghost artifacts through a sum of squares.

Figure 6:
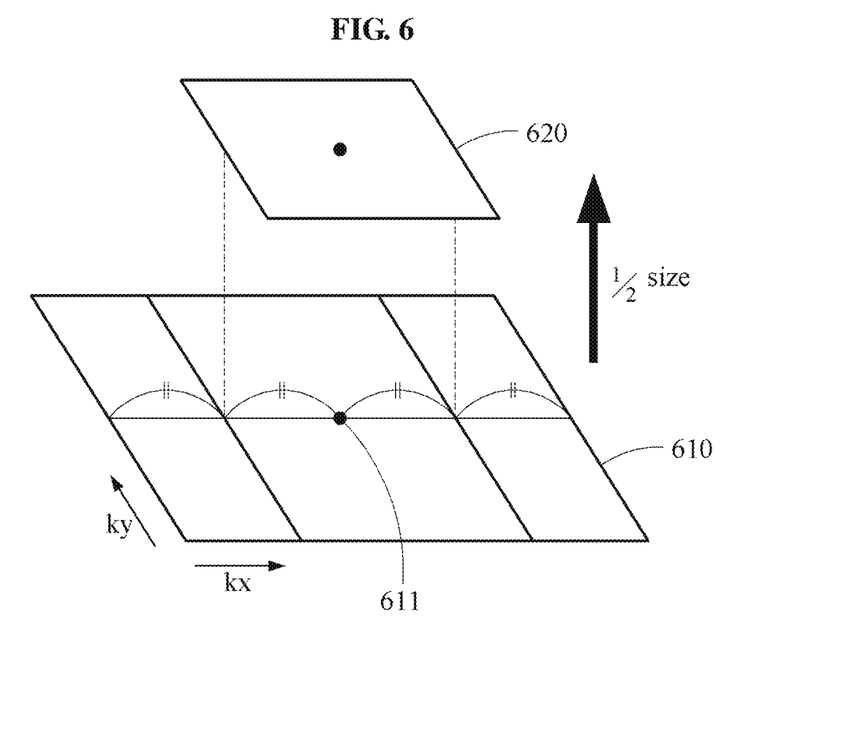
FIG. 6 illustrates a change in size of a reconstructed patch at each level of a pyramidal structure according to an embodiment.

FIG. 6 illustrates a change in size of a reconstructed patch at each level of a pyramidal structure according to an embodiment.

Referring to FIG. 6, a low rank completion algorithm may be calculated efficiently through a pyramid-structured scheme. The low rank completion algorithm may be calculated with respect to an independent patch. By using the pyramidal structure as shown in FIG. 6, a size of a patch may be reduced for each operation, and reconstruction may be performed differently based on a signal-to-noise ratio (SNR) for each operation, whereby a number of interactions of an iterative reconstruction-based low rank matrix completion algorithm may be reduced. Such a pyramidal structure may apply to a kx-ky domain.

A patch 610 in a first operation and a patch 620 in a second operation are illustrated. In this example, as advancing to a subsequent operation, an x-axial length of a patch may be reduced to half a length of a patch in a previous operation. Since a center 611 of each patch includes a low-frequency portion at all times, reconstruction may be performed more precisely without noise as advancing to a subsequent operation. Thus, a number of iterations of a low rank matrix completion algorithm may decrease, and reconstructed data of a previous operation may be used as an initial value of each operation, whereby more accurate result values may be obtained.

In another example, a length and a width of a patch may be reduced to those of a patch in a previous operation.

Figure 7:
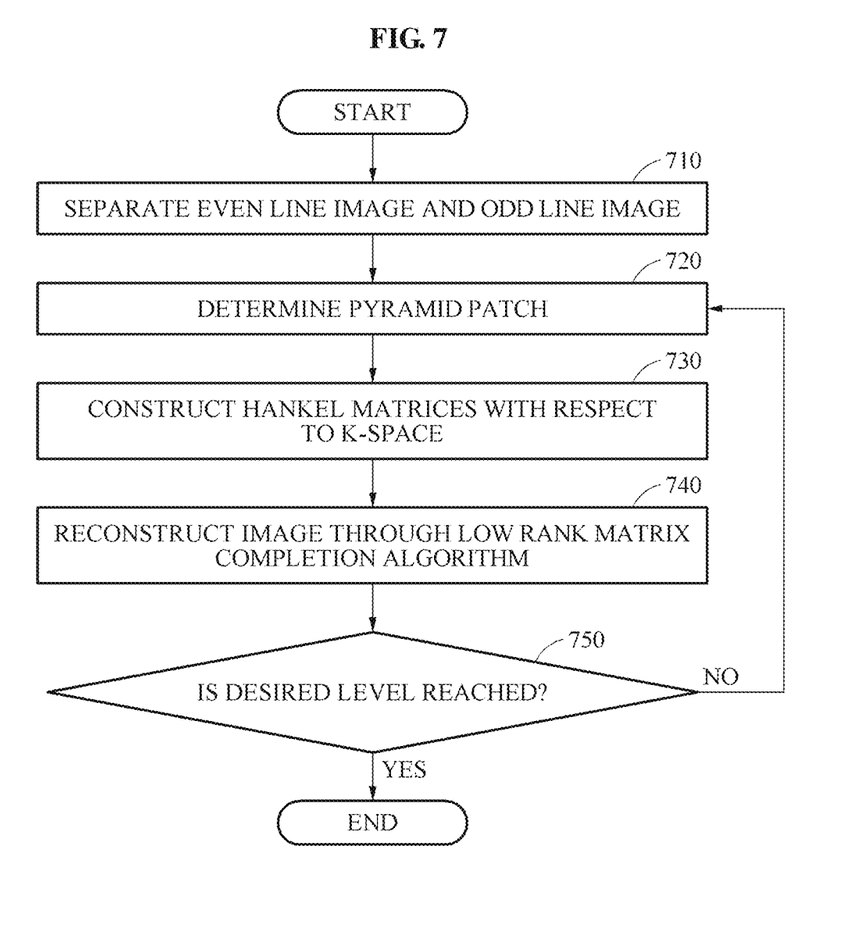
FIG. 7 is a flowchart illustrating a reconstruction process to which a pyramidal structure is applied according to an embodiment.

FIG. 7 is a flowchart illustrating a reconstruction process to which a pyramidal structure is applied according to an embodiment.

In operation 710, an apparatus for reconstructing a magnetic resonance image may separate an even scan line image and an odd scan line image from a k-space of an EPI image.

In operation 720, the apparatus for reconstructing a magnetic resonance image may determine a pyramid patch. The apparatus for reconstructing a magnetic resonance image may reconstruct the even scan line image and the odd scan line image through a matrix completion algorithm, and reduce a size of the pyramid patch.

In operation 730, the apparatus for reconstructing a magnetic resonance image may construct Hankel matrices of the k-space from the even scan line image and the odd scan line image.

In operation 740, the apparatus for reconstructing a magnetic resonance image may reconstruct an image through a low rank matrix completion algorithm. The apparatus for reconstructing a magnetic resonance image may reconstruct a low-frequency domain of the k-space through the matrix completion algorithm using values of the restored even scan line image and the restored odd scan line image as initial values.

In operation 750, the apparatus for reconstructing a magnetic resonance image may determine whether a pyramid level reaches a desired level.

In this example, operations 720 through 740 may be iteratively performed until the pyramid level reaches the desired level while reducing a size of a patch to half a size of a previous patch that is yet to undergo operation 750.

In a reconstruction process to which a pyramidal structure is applied, reconstruction may be performed differently based on an SNR for each level and for each operation, whereby a number of interactions of an iterative reconstruction-based low rank matrix completion algorithm may be reduced.

Figure 8A:
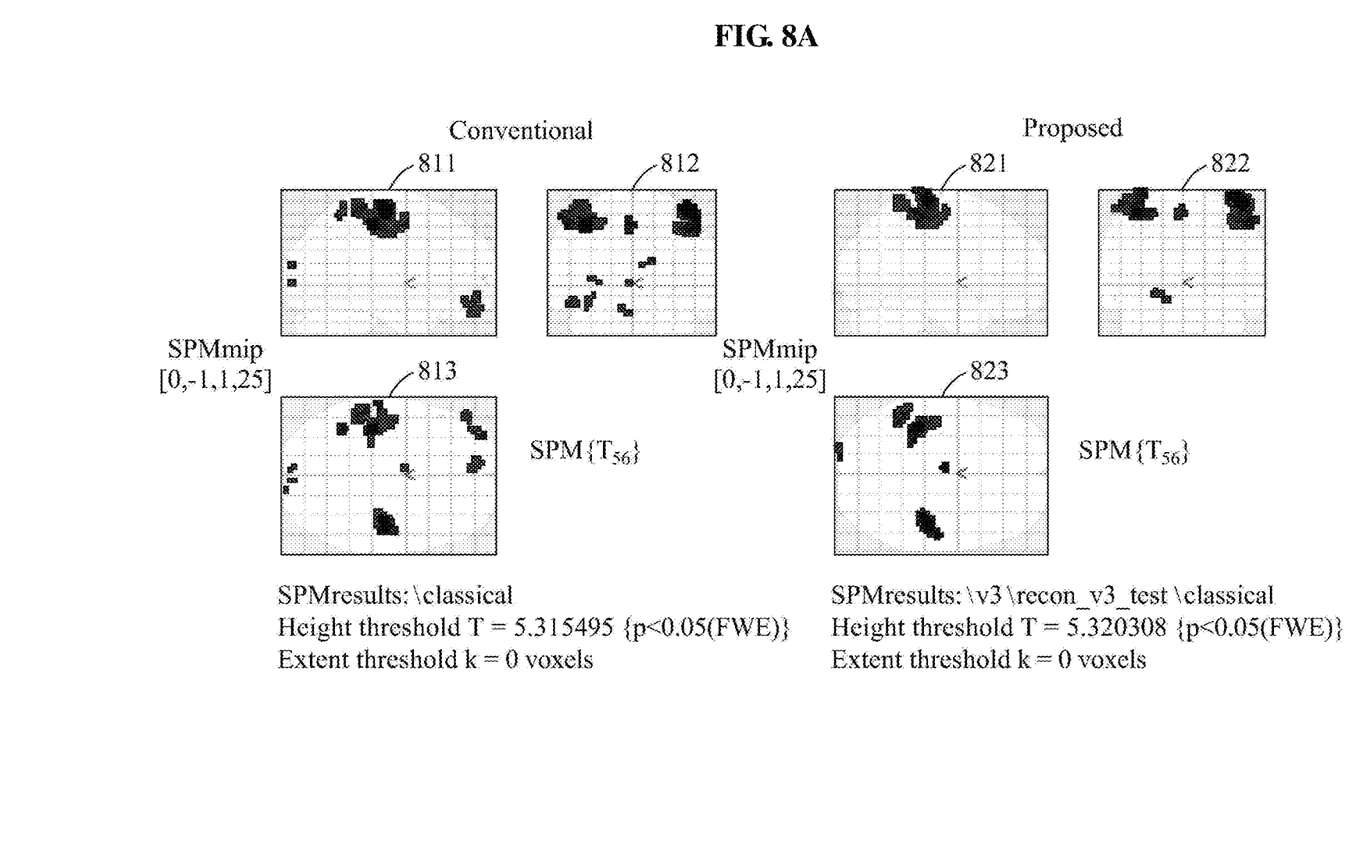
FIGS. 8A and 8B illustrate results of a method of reconstructing a magnetic resonance image according to an embodiment.
Figure 8B:
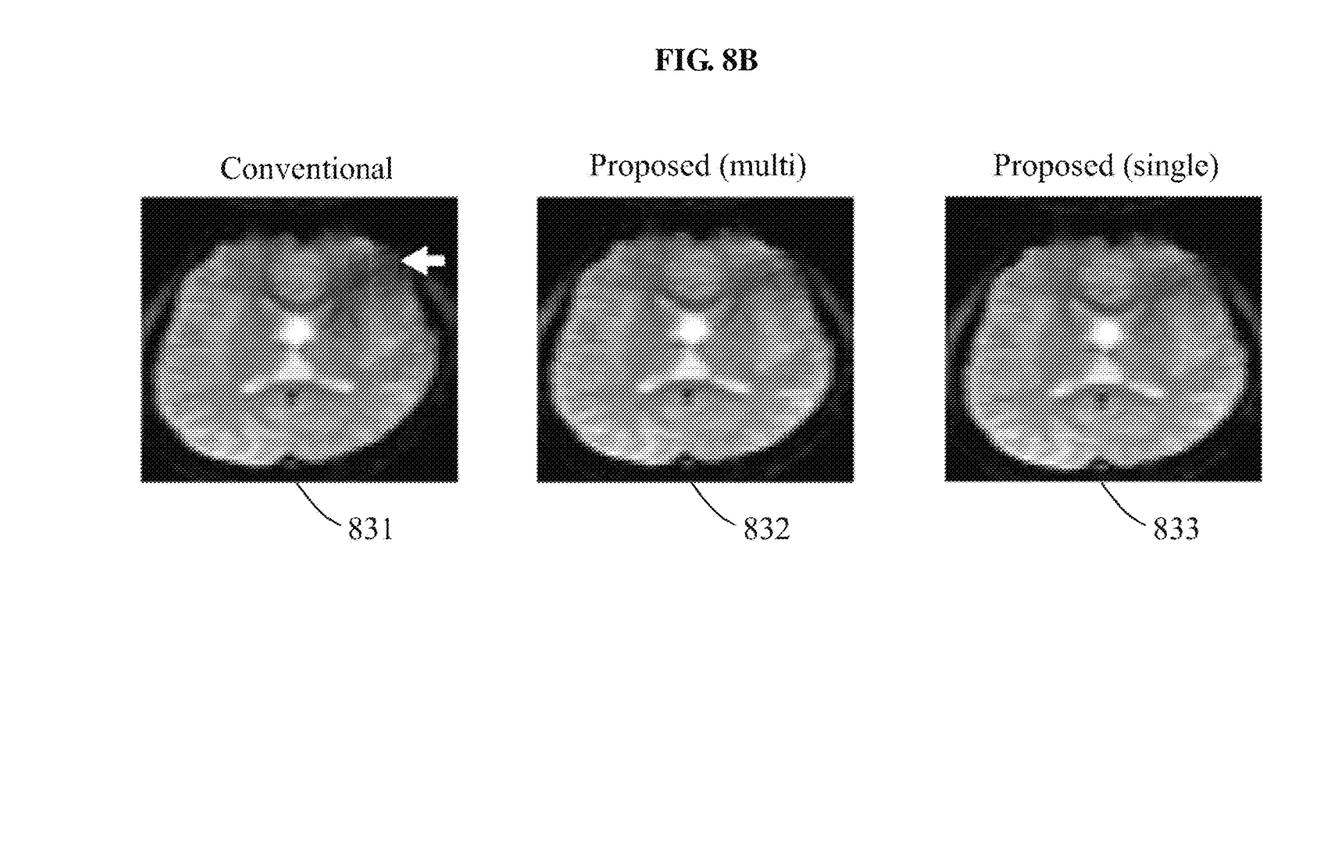

FIGS. 8A and 8B illustrate results of a method of reconstructing a magnetic resonance image according to an embodiment.

Referring to FIG. 8A, magnetic resonance images viewed from a side 811, a front 812, and a top 813 according to a conventional or related art include ghost artifacts, whereas magnetic resonance images viewed from a side 821, a front 822, and a top 823 according to an embodiment do not include ghost artifacts.

Referring to FIG. 8B, a magnetic resonance image 831 according to a conventional or related art includes ghost artifacts (pointed by an arrow), whereas magnetic resonance images according to an embodiment, in detail, both a single-coil image 832 and a multi-coil image 833, do not include ghost artifacts.

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such as parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described embodiments may be recorded in non-transitory computer-readable media including program instructions to implement various operations of the above-described embodiments. The media may also include, alone or in combination with the program instructions, data files, data structures, and the like. The program instructions recorded on the media may be those specially designed and constructed for the purposes of embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described embodiments, or vice versa.

A number of embodiments have been described above. Nevertheless, it should be understood that various modifications may be made to these embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claim.

The invention claimed is:

1. A method of reconstructing a magnetic resonance image, the method comprising:
    receiving echo planar imaging (EPI) data;
    acquiring an even scan line image and an odd scan line image from k-space data of the EPI data; and
    reconstructing missing portions of the even scan line image and the odd scan line image;
    wherein the reconstructing of the missing portions of the even scan line image and the odd scan line includes one or more of the following:
        reconstructing the missing portions by constructing block Hankel matrices from the even scan line image and the odd scan line image based on a presence of an annihilation filter in a k-space and interpolating Fourier data yet to be measured through a low rank matrix completion algorithm;
        reconstructing the even scan line image and the odd scan line image using a plurality of minimum rank matrix completion algorithms after changing pyramid patches, each having a pyramidal structure, into block Hankel matrices; and
        assigning a weighting to a k-space of each of the even scan line image and the odd scan line image and constructing block Hankel matrices from the weighted even scan line image and the weighted odd scan line image.

2. The method of claim 1, wherein the reconstructing of the missing portions by constructing the block Hankel matrices from the even scan line image and the odd scan line image is performed by reconstructing the missing portions by constructing block Hankel matrices from the even scan line image and the odd scan line image based on the presence of the annihilation filter in the k-space and interpolating Fourier data yet to be measured through the low rank matrix completion algorithm, and further comprises transforming the even scan line image and the odd scan line image into the block Hankel matrices using a commutative rule of a convolution operation of the k-space and the annihilation filter in a frequency domain.

3. The method of claim 1, further comprising:
    generating a single reconstructed image by combining the reconstructed even scan line image and the reconstructed odd scan line image.

4. The method of claim 3, wherein the generating of the single reconstructed image comprises generating the single reconstructed image using a sum of squares of the reconstructed even scan line image and the reconstructed odd scan line image.

5. The method of claim 1, wherein the reconstructing of the even scan line image and the odd scan line image is performed by reconstructing the even scan line image and the odd scan line image using the plurality of minimum rank matrix completion algorithms after changing pyramid patches, each having the pyramidal structure, into block Hankel matrices and further comprises reconstructing the even scan line image and the odd scan line image through the matrix completion algorithms, reducing sizes of the pyramid patches, and reconstructing a low-frequency domain of a k-space through the matrix completion algorithms using values of the reconstructed even scan line image and the reconstructed odd scan line image as initial values.

6. The method of claim 1, wherein the reconstructing of the even scan line image and the odd scan line image comprises applying a stop reference less than or equal to a preset reference to a pyramid patch including noise greater than or equal to the preset reference, and applying a stop reference greater than or equal to the preset reference to a pyramid patch from which a low-frequency domain is cut off, among the pyramid patches, each having the pyramidal structure.

7. The method of claim 1, wherein the EPI data comprises at least one of single-coil EPI data or multi-coil EPI data.

8. A computer program combined with hardware and stored in a non-transitory computer-readable storage medium to cause a computer to perform the method of claim 1.

9. An apparatus for reconstructing a magnetic resonance image, the apparatus comprising:
    a processor configured to acquire an even scan line image and an odd scan line image from k-space data of echo planar imaging (EPI) data, and reconstruct missing portions of the even scan line image and the odd scan line image;
    wherein the processor is configured to reconstruct the missing portions by one or more of the following:
        constructing block Hankel matrices from the even scan line image and the odd scan line image based on a presence of an annihilation filter in a k-space and interpolating Fourier data yet to be measured through a low rank matrix completion algorithm;
        using a plurality of minimum rank matrix completion algorithms after changing pyramid patches, each having a pyramidal structure, into block Hankel matrices; and
        assigning a weighting to the k-space of each of the even scan line image and the odd scan line image and constructing block Hankel matrices from the weighted even scan line image and the weighted odd scan line image.

10. The apparatus of claim 9, wherein the processor is configured to reconstruct the missing portions by constructing block Hankel matrices from the even scan line image and the odd scan line image based on the presence of the annihilation filter in the k-space and interpolating Fourier data yet to be measured through the low rank matrix completion algorithm and further configured to transform the even scan line image and the odd scan line image into the block Hankel matrices using a commutative rule of a convolution operation of the k-space and the annihilation filter in a frequency domain.

11. The apparatus of claim 9, wherein the processor is configured to generate a single reconstructed image by combining the reconstructed even scan line image and the reconstructed odd scan line image.

12. The apparatus of claim 11, wherein the processor is configured to generate the single reconstructed image using a sum of squares of the reconstructed even scan line image and the reconstructed odd scan line image.

13. The apparatus of claim 9, wherein the processor is configured to reconstruct the even scan line image and the odd scan line image by using the plurality of minimum rank matrix completion algorithms after changing the pyramid patches, each having the pyramidal structure, into block Hankel matrices, and through the matrix completion algorithms, reduce sizes of the pyramid patches, and reconstruct a low-frequency domain of a k-space through the matrix completion algorithms using values of the reconstructed even scan line image and the reconstructed odd scan line image as initial values.

14. The apparatus of claim 9, wherein the processor is configured to apply a stop reference less than or equal to a preset reference to the pyramid patch including noise greater than or equal to the preset reference, and apply a stop reference greater than or equal to the preset reference to pyramid patch from which a low-frequency domain is cut off, among the pyramid patches, each having the pyramidal structure.

\* \* \* \* \*